United States Patent [19]

Scates et al.

[11] Patent Number: 5,466,874
[45] Date of Patent: Nov. 14, 1995

[54] POLYMERIC CARBONYLATION CATALYST SYSTEM

[75] Inventors: Mark O. Scates, Pearland; R. Jay Warner; G. Paull Torrence, both of Corpus Christi, all of Tex.

[73] Assignee: Hoechst Celanese Corporation, Somerville, N.J.

[21] Appl. No.: 110,999

[22] Filed: Aug. 24, 1993

Related U.S. Application Data

[62] Division of Ser. No. 938,787, Aug. 31, 1992, Pat. No. 5,281,359.
[51] Int. Cl.$^6$ .............................. C07C 51/12; C07C 53/08
[52] U.S. Cl. ..................... 562/519; 562/521; 562/522
[58] Field of Search ................................ 562/519, 521, 562/522; 502/102, 230, 262, 330, 440

[56] References Cited

U.S. PATENT DOCUMENTS

| | | | |
|---|---|---|---|
| 3,769,329 | 10/1973 | Paulik et al. | 260/488 K |
| 3,855,307 | 12/1974 | Rony et al. | 562/519 X |
| 4,066,705 | 1/1978 | Hughes | 260/604 HP |
| 4,419,490 | 12/1983 | Bayer et al. | 525/61 |
| 4,667,053 | 5/1987 | Lin | 560/204 |
| 5,001,259 | 3/1991 | Smith et al. | 562/519 |
| 5,026,908 | 6/1991 | Smith et al. | 562/519 |
| 5,131,943 | 7/1992 | Allison et al. | 75/426 |
| 5,155,261 | 10/1992 | Marston et al. | 562/519 |
| 5,250,489 | 10/1993 | Della Betta et al. | 502/262 |
| 5,258,349 | 11/1993 | Della Betta et al. | 502/330 |
| 5,259,754 | 11/1993 | Della Betta et al. | 502/262 |
| 5,334,755 | 8/1994 | Yoneda et al. | 562/519 |

FOREIGN PATENT DOCUMENTS

| | | |
|---|---|---|
| 0277824 | 8/1988 | European Pat. Off. . |
| 1108088 | 12/1982 | U.S.S.R. . |

OTHER PUBLICATIONS

"Acetic Acid by Low Pressure Carbonylation of Methanol with a Supported Rhodium Catalyst", by Wing S. Fong, *Process Economics Program*, Menlo Park, Calif., Feb. 1990, pp. 1–14.
"A Novel Copolymer–Bound Cis–Dicarbonylrhodium Complex for the Carbonylation of Methanol to Acetic Acid and Acetic Anhydride", Yuan Guoqing et al, *Chinese Journal of Polymer Science*, vol. 7, No. 3, 1989, pp. 219–224.
"Kinetic Study of Carbonylation of Methanol to Acetic Acid and Acetic Anhydride Over a Novel Copolymer–Bound CIS–Dicarbonylrhodium Complex", Chen Yuying et al, *Chinese Journal of Polymer Science*, vol. 7, No. 3, 1989, pp. 225–231.
"Design and Synthesis of a Solid Bifunctional Polymer Catalyst for Methanol Carbonylation", K. M. Webber et al, *Journal of Molecular Catalysis*, 3 (1977/78), pp. 1–9.
"Ionic Attachment as a Feasible Approach to Heterogenizing Anionic Solution Catalysts. Carbonylation of Methanol", R. S. Drago et al, *Inorganic Chemistry*, American Chemical Society, vol. 20, No. 3, Mar. 1981, pp. 641–644.
"Methanol Carbonylation Catalyzed by a Polymer–Bound Rhodium (I) Complex", M. S. Jarrell et al, *Journal of Catalysis*, 40, 1975, pp. 255–267.
"Methanol Carbonylation Catalyzed by Polymer–Supported Rhodium Complexes", *Applied Catalysis*, 35, (1987), pp. 279–288.
CA112 (12): 1011116d (1989).
CA112 (11): 98064c (1989).
CA109 (2): 839v (1989).
CA91 (14): 112972d (1979).
CA89 (11): 90020w (1978).
CA117 (6): 51254c (1992).
CA114 (25): 246784w (1989).
CA114 (25): 246530k (1989).
CA114 (12): 104708a (1989).
CA112 (26): 237139w (1989).
CA109 (9): 72943b (1987).
CA108 (18): 152558z (1986).
CA107 (25): 236050v (1987).
CA106 (23): 195856w (1985).
CA101 (23): 21057s (1982).
CA99 (2): 6232t (1981).
CA98 (15): 125509c (1983).
CA97 (4): 25529v (1980).
CA95 (16): 139381e (1981).
CA91 (15): 123409b (1977).
CA90 (7): 54480h (1977).
CA88 (2): 8078u (1977).
CA84 (15) 104661s (1975).

Primary Examiner—Arthur C. Prescott
Attorney, Agent, or Firm—Stuart D. Frenkel; Donald R. Cassady

[57] ABSTRACT

A carbonylation catalyst useful for the carbonylation of methanol to acetic acid, acetic anhydride or both comprises a polymer support containing pendant pyrrolidone groups which support a rhodium species. Other polymeric supports capable of withstanding carbonylation temperatures of at least 150° C. are disclosed for the carbonylation reaction in which rhodium levels in the reaction medium of greater than 500 ppm are contemplated.

25 Claims, No Drawings

POLYMERIC CARBONYLATION CATALYST SYSTEM

This application is a division, of application Ser. No. 07/938,787, filed Aug. 31, 1992 now U.S. Pat. No. 5,281,359.

The present invention is directed to a novel catalyst useful in the carbonylation of methanol to acetic acid, carbonylation of methyl acetate to acetic anhydride or both. The invention is also concerned with a method of carbonylating lower alcohols, esters or ethers to carboxylic acids, acid anhydrides or both in the presence of a rhodium-containing catalyst.

Among currently-employed processes for synthesizing acetic acid, one of the most useful processes commercially is the rhodium-catalyzed carbonylation of methanol with carbon monoxide as taught in U.S. Pat. No. 3,769,329, issued to Paulik et al on Oct. 30, 1973, and known as the "Monsanto process". Although the Paulik et al patent discloses that the rhodium catalyst can be used dissolved or otherwise dispersed in the liquid medium or else supported on an inert solid, commercially, the catalyst is utilized in a homogeneous reaction system in which the rhodium catalyst is dissolved in the reaction solvent which typically is acetic acid. The homogeneous catalyst system also includes a halogen-containing catalyst promoter as exemplified by methyl iodide. The reaction is conducted by continuously bubbling carbon monoxide gas through the liquid reaction medium.

Paulik et al teach that the liquid reaction medium can include any solvent compatible with the catalyst system and that it may comprise, for example, the pure alcohol which is being reacted or mixtures thereof with the desired carboxylic acid end product and/or esters of these two compounds. The preferred solvent and liquid reaction medium for the process is the desired carboxylic acid itself, i.e., acetic acid when methanol is being carbonylated to produce acetic acid.

The Paulik et al patent also discloses that the addition of water enhances the reaction rate of the carbonylation of the alcohol to the carboxylic acid. Accordingly, commercial formation of acetic acid using the Monsanto process technology as disclosed in Paulik et al utilize over 14 to 15 wt. % water in the reaction medium. This has been characterized as the "high water" carbonylation process. Unfortunately, recovering acetic acid in anhydrous or nearly anhydrous form from such an appreciable quantity of water involves substantial expenditure of energy in distillation and/or additional processing steps such as solvent extraction, as well as requires larger purification process equipment as compared with that used in purifying carboxylic acid containing significantly lower quantities of water. Thus, while reactor output of acetic acid is highly efficient at high reactor water concentrations, production capacity is typically limited by water removal capability from the acetic acid product.

An improvement over the high water Monsanto process for the carbonylation of an alcohol to produce a carboxylic acid having one carbon atom more than the alcohol in the presence of a rhodium catalyst has been developed by Hoechst Celanese and is disclosed in commonly assigned U.S. Pat. No. 5,001,259, issued Mar. 19, 1991, and U.S. Pat. No. 5,026,908, issued Jun. 25, 1991, and copending application U.S. Ser. No. 615,846, filed Nov. 20, 1990. As disclosed therein, acetic acid is produced from methanol in a homogeneous reaction medium comprising methyl acetate, methyl halide, especially methyl iodide, and rhodium present in a catalytically-effective concentration. The invention therein resides primarily in the discovery that catalyst stability and the productivity of the carbonylation reactor can be maintained at surprisingly high levels, even at low water concentrations, i.e. below 14 wt. % and even at 10 wt. % and substantially less, in the reaction medium (despite the general industrial practice of maintaining approximately 14 wt. % or 15 wt. % water). The Hoechst Celanese process has been characterized as the "low water" carbonylation process and yields substantially higher rates of production over the high water process since reactor productivity is maintained relative to the high water process and at the same time recovery of the dry acid product is substantially easier (i.e., less energy consumption, smaller equipment, lower rhodium usage) in view of the low water levels. These results are achieved by maintaining in the reaction medium, along with a catalytically-effective amount of rhodium, at least a finite concentration of water, methyl acetate and methyl iodide, a specified concentration of iodide ions over and above the iodide content which is present as methyl iodide or other organic iodide. The iodide ion is present as a simple salt, with lithium iodide being preferred. The concentrations of methyl acetate and iodide salts are significant parameters in affecting the rate of carbonylation of methanol to produce acetic acid especially at the low reactor water concentrations. By using relatively high concentrations of the methyl acetate and iodide salt, one obtains a surprising degree of catalyst stability and reactor productivity even when the liquid reaction medium contains water in concentrations as low as about 0.1 wt. %, so low that it can be broadly defined simply as "a finite concentration" of water. Furthermore, the reaction medium employed improves the stability of the rhodium catalyst, i.e. resistance to catalyst precipitation, especially during the product-recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. Pat. Nos. 5,001,259 and 5,026,908 and copending application U.S. Ser. No. 615,846 are herein incorporated by reference.

While the "low water" carbonylation process described immediately above has been successful at greatly increasing the production rate for acetic acid, such process still poses several problems. For one, as the water level in the reaction mixture is decreased, the instability and, thus, precipitation of the rhodium catalyst increases. Accordingly, the amount of lithium iodide stabilizer which must be added has to be increased. It has further been found the acetic acid product which is formed contains minute quantities of impurities which can adversely affect the quality of the acetic acid product as determined by permanganate time. Post-treatment of the acetic acid product has been able to remove the impurities but such processes merely add additional cost to the process and bottle-neck production.

As an alternative to the commercial homogeneous catalyst systems employed, attempts have been made to utilize a heterogeneous rhodium catalyst in the carbonylation of methanol to acetic acid. Advantages of such a catalyst system include the easy separation of the rhodium from the reaction products as well as the desire to prevent precipitation or scaling of the rhodium from the reaction system as results in the homogeneous catalyst system. Reducing loss of the rhodium catalyst by precipitation and/or scaling and the like is very advantageous in view of the high cost of replacing the rhodium. It is not believed that such attempts have been very successful, however, and it is not known whether there has been any commercial application utilizing heterogeneous catalyst systems in the rhodium-catalyzed carbonylation of methanol to acetic acid.

Examples of suggested use of heterogeneous catalysts include European Patent Application 277,824, published Aug. 10, 1988, and assigned to Reilly Tar and Chemical Corp., which discloses the carbonylation of methanol to acetic acid utilizing rhodium supported on a heterogeneous polymer support which comprises poly(4-and 2-vinyl pyridine) copolymers. In particular, Reilex® copolymers, manufactured by the assignee of the application, are preferred and comprise pyridine rings attached directly at their 2- or 4-positions to the polymer backbone which in turn is cross-linked with a small amount of divinylbenzene. For reaction, presumably the copolymer or N-oxide of the copolymer is quaternized with an alkyl halide such as methyl iodide and loaded by reaction with a rhodium salt. A better than 6-fold increase in catalyst activity was described as being found in European Patent Application 277,824 over reported and calculated values for the homogeneous Monsanto process. However, actual side by side comparisons of the homogeneous catalyst with the heterogeneous catalyst described in the European patent application have shown roughly comparable activity using the heterogeneous catalyst relative to the high water Monsanto process, but the 6-fold increase as suggested has not been duplicated.

Earlier attempts to form a heterogeneous catalyst for the rhodium-catalyzed carbonylation of methanol to acetic acid include that of Jarrell and Gates, *Journal of Catalysis*, 40, 255–267, (1975) wherein a styrene-divinylbenzene copolymer containing diphenyl phosphine groups was used to support rhodium for both liquid and gas phase reaction. Similarly, Webber, Gates and Drenth, *Journal of Molecular Catalysis*, 3 (1977/78) 1–9, also discloses a bifunctional polymer for rhodium catalysis of the methanol carbonylation reaction. The polymer was a lightly cross-linked polystyrene containing attached rhodium complexes and also containing attached groups analogous to pentachlorothiophenol which latter groups served both to coordinate the rhodium to the polymer and to undergo oxidative addition with rhodium in a step analogous to that involving rhodium and the soluble promoter in the solution reaction. It was thought that the bound promoter would coordinate the rhodium so strongly that problems of separation, corrosion and loss of the expensive rhodium could be alleviated. However, it was found that there was rhodium loss and the lack of stability of the bifunctional polymeric catalyst The possibility of supporting a rhodium compound on an ionic resin such as Dowex 1-XB, Bio-Rex 9, or a possible copolymer of styrene and 4-vinylpyridine alkylated with methyl iodide has been described by Drago et al, *Inorg. Chem.*, 20, 641–644 (1981). This article included no experimental results using the suggested polyvinylpyridine derivative catalyst. From the examples that were given, the authors concluded that their ionically-supported rhodium catalyst was approximately equal in catalytic activity to the homogeneous complex, and that leaching of the catalyst could be minimized by suitable choice of solvent and by selecting high resin to rhodium ratios. In all tests reported, however, only low temperatures of 120° C. and low pressures of 80 psi were used. Moreover, it was believed that doubling the amount of supported catalyst (and thus the rhodium present) resulted in a corresponding doubling of the reaction rate, and that an effective method of carrying out the reaction may be to maintain large concentrations of catalyst particularly in a liquid-flow system design.

In a later-issued U.S. Pat. No. 4,328,125, Drago et al similarly used only mild temperatures at about 120°–130° C. and pressures ranging from less than 60 psi to 160 psi in one example to carbonylate methanol with a rhodium heterogeneous catalyst. These conditions, and particularly the low temperatures, are wholly impractical for any commercial use in acetic acid production, and are specifically far outside the Monsanto process conditions of temperature which ranges from about 170°–200° C. As a result, the reaction rates are so low as compared to the homogeneous process that large reactors with increased material costs, long residence times, and resulting low space-time yields would be needed to have any hope of producing a commercial product. These mild Drago et al conditions are nonetheless required by most ion exchange resins which are not stable, for example, at sustained elevated temperatures above 130° C. and approaching 170° C. Thus, at conditions of carbonylation of at least about 170° C., the catalyst should be stable and not form substantial amounts of degradation products for at least about 6 months to be commercially viable. The patent concludes that large concentrations of catalysts relative to liquid, particularly in a flow process, will result in very rapid reaction rates with the process preferably being carried out at these lower temperatures under less corrosive conditions than processes using conventional homogeneous catalysts. Although polyvinylpyridines, as such, are mentioned at one point in the Drago et al patent, no examples are given of their preparation or use. The examples are instead limited to one example of a polystyrene bound pyridine and to commercially available anionic exchange resins identified as Amberlite 1RA-400 and Dowex 1-XB which have been used as catalysts for the hydroformylation of olefins.

There are still additional examples of utilizing polymeric supports for rhodium catalysts used in the carbonylation of methanol to acetic acid. Soviet Union Patent 1,108,088 utilizes a complex of rhodium with polyethylene oxide and an alkyl halide promoter to manufacture acetic acid by carbonylating methanol. Yuan et al, *Chinese Journal of Polymer Science*, Vol 7, No. 3, 1989, page 219, carbonylated methanol to acetic acid by complexing rhodium with ethylene diacrylate-crosslinked copolymers of 2-vinylpyridine and methyl acrylate. Rhodium has also been complexed with other polymeric supports for the hydroformylation of an olefin to an aldehyde or alcohol. An example of such is U.S. Pat. No. 4,066,705 wherein rhodium is complexed with a polybenzimidazole fiber support.

U.S. Pat. No. 4,667,053 discloses the carbonylation of olefins to esters utilizing a heterogeneous palladium/copper catalyst on a polymer support which can include a polyvinylpyrrolidone, polyvinylpyridine and polyvinylpyridine copolymers with styrene.

Although various heterogeneous catalyst systems have been proposed for the rhodium-catalyzed carbonylation of methanol to acetic acid, at the present time it is not known whether there exists any commercial reactors utilizing such technology. One reason for this is that the heterogeneous catalyst systems have been found to be relatively unstable. Prior art polymeric catalyst systems suffer from chemical, thermal, and physical stability problems at commercially viable carbonylation reaction conditions.

Increased rhodium levels are known to provide increased catalytic activity and increased production of acetic acid in the reactor and, rhodium levels of up to 1,000 ppm have been disclosed in aforementioned commonly assigned patents U.S. Pat. No. 5,001,259 and U.S. Pat. No. 5,026,908. However, the use of rhodium levels of 500 ppm and above have not been used on a commercial scale. There are several practical reasons for limiting the rhodium levels in the reactor. For one, the increased amount of rhodium results in precipitation problems regardless of the reactor water concentration although at the low water concentrations, the precipitation problem with rhodium levels of 500 ppm and above are substantially more pronounced. Under the low water conditions, a substantial amount of iodide salt stabilizer, typically 10% and above is required to control rhodium precipitation. In the high water process, increased rhodium levels also lead to precipitation problems and even if such problems can be alleviated, the increased reactor output cannot be accommodated downstream where the water must be removed from the acetic acid product. The heterogeneous system disclosed in European Patent Application 277,824, discussed above, only contemplated using rhodium levels below 500 ppm based on the reaction system. It is known to carbonylate methyl acetate to make acetic anhydride using rhodium catalyst levels substantially above 1,000 ppm. However, to stabilize the homogeneous rhodium catalyst requires greater than 10% of a stabilizer which is typically a phosphine-type monodentate ligand. Obviously, the need to use increased amounts of the stabilizer increases the cost of the process with respect to starting materials as well as in purifying costs.

Accordingly, an important object of the present invention is to provide a process for the rhodium-catalyzed carbonylation of methanol to acetic acid, carbonylation of methyl acetate to acetic anhydride or coproduction in which in the reactivity of the catalyst can be greatly improved without the need for substantial levels of stabilizing salts and in which overall productivity can still be maintained.

SUMMARY OF THE INVENTION

It has now been found that the carbonylation of alcohols, esters and ethers to acids, anhydrides or both can be favorably achieved utilizing a polymeric catalyst support which tightly binds the rhodium catalyst. The polymeric support may be liquid, solid, homogeneous or heterogeneous with respect to the reaction medium. The polymeric supports are capable of providing stabilized rhodium levels in amounts greater than 500 ppm in the reaction medium and so bind the rhodium that under low water carbonylation conditions the amount of iodide stabilizer can be substantially reduced, if not eliminated. A particular useful catalyst comprises an insoluble polymer having pendent pyrrolidone groups which support the rhodium species. The most preferred catalyst is a slightly crosslinked polyvinylpyrrolidone which is loaded with a rhodium salt either in the reactor or as a preformed material.

By utilizing the polymeric catalyst of the present invention under the low water conditions as set forth in previous U.S. Pat. No. 5,001,259, the commercial process would realize the advantage of low energy consumption, smaller operating equipment and lower by-product yields (i.e., organic iodides, carbonyls and unsaturated organics). The polymeric catalyst of this invention firmly holds the rhodium on the support and, thus, less rhodium losses are generated resulting in less rhodium usage. At the same time, inasmuch as the polymeric support can firmly hold the rhodium, higher rhodium loadings can be effected thus vastly improving the reactor output.

While the preferred catalyst utilizes a polyvinylpyrrolidone support, the invention in its broadest aspect is applicable to the use of polymer-supported rhodium catalysts in the low water carbonylation of methanol to acetic acid in which the polymer support contains any atom which contains an unshared electron pair and can form an ionic complex with rhodium and is thermally and chemically stable at commercially viable carbonylation conditions. Thus, any polymer support which contains a nitrogen, phosphorus or a sulfur atom in its backbone, and, more preferably, pendent to the backbone and exhibits adequate thermal and chemical stability at commercially viable carbonylation conditions can be used in the low water carbonylation and would be believed to offer all the advantages described above.

DESCRIPTION OF THE PREFERRED EMBODIMENTS

The present invention is primarily concerned with an improved polymeric catalyst for use in the carbonylation of methanol or methyl acetate to form acetic acid and as well operating under anhydrous conditions to form acetic anhydride or to coproduce acetic acid and acetic anhydride. The catalyst of this invention comprises polymer support which contains multiple sites each of which sites can bind in any manner an alkyl iodide and rhodium species. The polymer support can be liquid or solid, and be either soluble or insoluble in the reaction medium. Thus, the polymeric support can be homogeneous with the liquid reaction medium or comprise a heterogeneous species either as a liquid such as a dispersed liquid or as a solid. The polymer support must be chemically and thermally stable under the typical operating conditions of carbonylation, in particular, at sustained temperatures of 150° C. and above and, preferably, at 175–225° C. For commercial viability, the polymer should be stable at the above elevated temperatures for at least 6 months and, most preferably, for at least 1 year. The polymer support should be capable of effectively binding sufficient rhodium to provide greater than 500 ppm rhodium in the reaction medium and/or sufficiently bind the rhodium to allow reduction in the iodide salt stabilizer under the low water conditions to below 10 wt. % while providing a rhodium content of 300–500 ppm.

A preferred polymer support is an insoluble polymer having pendent pyrrolidone groups which support the rhodium species. The most preferred catalyst is a polyvinylpyrrolidone which has been crosslinked and rhodium loaded as described above. Cross-linking can be achieved using a caustic catalyst as disclosed in U.S. Pat. No. 2,938,017 or by using a cross-linking agent such as disclosed in German 2,059.484. These references are herein incorporated by reference. This preferred catalyst is prepared by reacting the polymer support with an alkyl halide and a rhodium compound. Both reactions are readily accomplished by standard procedures and using known components for such reactions. For example, it is preferred to simply add an amount of the insoluble polymer such as in powder or resin bead form to what otherwise constitutes as the homogeneous medium for the methanol carbonylation reaction. Such carbonylation reaction medium includes methanol and/or methyl acetate, acetic acid and a small amount of water in a pressure vessel along with a rhodium compound and an iodide promoter. The preferred promoter for the manufacture os acetic acid and derivatives is methyl iodide. Rhodium triiodide and rhodium acetate are the rhodium compounds of choice, although other suitable compounds are known and available.

In addition to the polyvinylpyrrolidone polymers as described above, other polymers can be used to support the rhodium metal catalyst and find particular use in the heterogeneous carbonylation of methanol to acetic acid, acetic anhydride or coproduction of these materials under high rhodium loadings, i.e., >500 ppm and/or the low water conditions developed by Hoechst Celanese. Thus, the polyvinylpyridine copolymers as described in European Patent 277,824 and commercially available under the tradename of Reillex® from Riley Tar and Chemical Corporation of Indianapolis, Ind., may be useful. Still further, polymeric systems which contain any phosphorus, sulfur or nitrogen group which can be complexed with an alkyl halide such as methyl iodide and the rhodium salt can be useful polymeric supports for the heterogeneous catalyst and find use in the desired carbonylation, in particular, under the low water carbonylation conditions. These groups are preferably contained in pendant chains to the backbone of the polymer but may be part of the backbone itself. In this regard, any suitable polymer which can be complexed with an alkyl halide and rhodium, and that is soluble (homogeneous) or insoluble in the reaction mixture (heterogeneous), whether the insolubility results from molecular weight, crosslinking by chemical, thermal or radiation means or some other technique or procedure is useful. Furthermore, such polymers must exhibit stability at the elevated temperatures in which the commercial carbonylation reaction is typically run as described previously. Another important feature is that the polymeric support contain an effective amount of the ionizable group sufficient to support and complex with the rhodium metal at necessary loading levels to provide a beneficial catalytic activity. Examples of other polymeric supports include those that contain pendent diaryl or dialkylphosphines, alkyl or aryl sulfides and sulfoxides off of a thermally stable vinyl backbone.

As described above, the polymer supports useful in this invention may be heterogeneous but, such catalysts may also be soluble or homogeneous in the carbonylation reaction medium. Thus, polymeric supports which are in the liquid state may be used as catalyst supports in the carbonylation reactions of this invention. Such liquid polymers typically are not highly cross-linked or have a lower molecular weight. Although the homogeneous polymeric catalysts will not have the advantage of the heterogeneous supports insofar as separation of rhodium catalyst from the reaction medium by physical means may not be readily achieved, the polymeric support in view of the multiplicity of binding sites contained therein will be able to bind sufficient rhodium to vastly increase rhodium levels in the reaction medium over the homogeneous systems used to date. Thus, it is expected that rhodium levels greater than 500 ppm are readily achievable utilizing polymer supports. Like the heterogeneous systems, the homogeneous polymeric supports must be able to withstand the continuous operating conditions of the carbonylation reaction including sustained temperatures of above 150° C. Other than the limitation that such polymers be stable at elevated temperatures for sufficient periods of time, there is no other limitation regarding the polymeric support other than that such polymers should be able to bind or complex with or otherwise capture the alkyl iodide promoter and the catalytic rhodium species. It is contemplated that these homogeneous polymeric catalysts can be useful either in the high water or low water carbonylation reactions. Like the heterogeneous system, it is contemplated that the homogeneous polymeric supports provide greater than 500 ppm rhodium in the reaction medium and/or under the low water carbonylation allow for reduced iodide salt stabilizer which needs to be incorporated for stabilizing the rhodium species.

The polymer-supported rhodium carbonylation catalyst of this invention can be used in the carbonylation of methanol under the standard high water carbonylation conditions as has been commercially practiced consistent with the teachings of Paulik et al, U.S. Pat. No. 3,769,329. Preferably, the catalysts of the present invention are used in the low water carbonylation of methanol as developed by Hoechst Celanese. The use of the low water technology with the polymeric catalyst has several advantages which have been enumerated above. Again, these advantages include the fact that the low amount of water greatly reduces the amount of equipment, energy and respective costs involved in separating the product from the reaction water. Additionally, inasmuch as the polymeric support binds the rhodium to the polymer matrix, the rhodium does not precipitate and scale on the reactor as in the prior homogeneous system. In this regard, the lithium iodide stabilizer which has been used in the low water process to avoid the precipitation of the rhodium can be substantially reduced, or totally eliminated. In view of the stability of the polymer for binding the rhodium catalyst, rhodium loadings can be increased and thus improve catalytic activity in the reactor. Still further, on using a heterogeneous polymer catalyst, recycling and regeneration of the catalyst is readily accomplished using known separation procedures such as by simply filtering the solid catalyst from the liquid reactants or decantation of a liquid catalyst from the reaction medium.

The low water carbonylation using a polymer-supported rhodium catalyst of this invention requires a liquid reaction medium which may include any compatible solvent such as pure alcohols, or mixtures of the alcohol feedstock and/or the desired carboxylic acid and/or esters of these two compounds. The preferred solvent and liquid reaction medium for the low water carbonylation process comprises the carboxylic acid product. Thus, in the carbonylation of methanol to acetic acid, the preferred solvent is acetic acid.

In the production of carboxylic acids in the low water process, water concentrations anticipated are below 14 wt. %, typically from between 0.1 to less than 14 wt. %, preferably below 12 wt. %, most preferably between 1 and 6 wt. % based on the liquid reaction medium. Water levels below 1 wt. % are useful, in particular for the production of anhydride or coproduction of acid and anhydride.

In accordance with the low water carbonylation process most useful in the present invention, the desired reaction rates are obtained even at low water concentrations by including in the reaction medium an ester which corresponds to the alcohol being carbonylated and the acid product of the carbonylation reaction. Optionally, an additional iodide ion which is over and above the iodide which is present as a catalyst promoter such as methyl iodide or other organic iodide can be included. Thus, in the carbonylation of methanol to acetic acid, the ester is methyl acetate and the additional iodide promoter is an iodide salt, with lithium iodide being preferred. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, can be used provided that the salt is sufficiently soluble in the reaction medium to provide the desired level of the iodide. The iodide salt can be a quaternary salt of an organic cation or the iodide salt of an inorganic cation. Preferably it is an iodide salt of a member of the group consisting of the metals of Group Ia and Group IIa of the periodic table as set forth in the "Handbook of Chemistry and Physics" published by CRC Press, Cleveland, Ohio, 1975–76 (56th edition). In particular, alkali metal iodides are useful, with lithium iodide being preferred.

While the additional iodide ion is an essential component in the prior low water homogeneous catalyst system, this component may be eliminated in the polymeric catalyst system of the present invention. However, some additional iodide ion may be useful to further promote the carbonylation reaction. Thus, levels of iodide salt, such as LiI, of 0 to less than 10 wt. % may be useful for such purpose. Alternatively, the catalyst of this invention may be added to a prior low water homogeneous reaction system to provide additional rhodium catalyst stabilizing sites. In this case, up to 20 wt. % LiI or other iodide salt may be needed to stabilize and promote the dissolved rhodium content as like any other low water homogeneous system as described in U.S. Pat. No. 5,001,259.

The carbonylation reaction may be carried out by intimately contacting the feed alcohol, ester or ether which is in the liquid phase, with gaseous carbon monoxide bubbled through a liquid reaction medium containing the rhodium catalyst dispersed within, halogen-containing promoter, alkyl ester, and any additional soluble iodide salt promoter, at conditions of temperature and pressure suitable to form the carbonylation product. Thus, when the feed is methanol, the halogen-containing promoting component will comprise methyl iodide (complexed with the polymer support) and the alkyl ester will comprise methyl acetate. The methyl acetate is present in amounts of from 0.5–30, preferably 1–5 wt. %, and the methyl iodide is present in amounts of from 5–20, and preferably 10–16 wt. %. The rhodium catalyst is present in amounts of from 200–5000 ppm rhodium. In the prior low water homogeneous system, rhodium levels were preferably at 400–600 ppm although in practice, rhodium levels were kept below 500 ppm. Using the polymeric catalyst, rhodium levels above 500 ppm, above 900 ppm and even from 1000 to 5000 ppm may be provided since rhodium precipitation is not a significant problem as it is with prior stabilized homogeneous systems. The high levels of rhodium significantly improve space-time yields.

Typical reaction temperatures for carbonylation will be approximately 150°–250° C., with the temperature range of about 175°–220° C. being the preferred range. The carbon monoxide partial pressure in the reactor can vary widely but is typically about 2–50 atmospheres.

The polymeric catalyst of this invention is not only useful when used as the sole catalyst for the carbonylation but may be mixed with the prior art homogeneous catalyst systems. Thus, if the polymeric catalyst is a solid or otherwise present as a heterogeneous phase in the reaction medium such catalyst may be used in combination with the prior art homogeneous catalyst to further enhance rhodium levels and reactor productivity. It may be useful in such admixed system under low water carbonylation conditions to add a small amount of iodide salt such as lithium iodide to stabilize the homogeneous catalyst. Additionally, the polymeric catalyst which is used may be both a mixture of heterogeneous polymeric catalyst and homogeneous polymeric catalyst. In such an instance, the rhodium would be tightly bound to the polymeric catalyst either in the insoluble or soluble form such that little if any additional iodide salt stabilizer would be needed.

For the purposes of illustrating the invention, reference will now be made to the examples below which are directed to specific instances of preparation and use of the polymeric catalyst of this invention. The examples are illustrative only and are not to be construed as limiting the invention to the specific embodiments shown therein.

EXAMPLE 1

In this example, a polyvinylpyrrolidone catalyst was prepared. Thus, 30.08 grams of a cross-linked polyvinylpyrrolidone, 100.0 grams of methanol, 188.4 grams of acetic acid, 75.4 grams of methyl iodide, 20.0 grams of water and 0.7011 gram $[Rh(acetate)_2]_2$ equivalent to 46.3% rhodium or 0.3246 gram of rhodium metal were added to a Hastelloy C autoclave stirred and heated to 190° C. for 2 hours. The polymer catalyst was filtered from the liquid reactants. The filtrate contained 0.001845 gram of unabsorbed rhodium. The rhodium loading on the polymer was determined by metal uptake and found to be 1.062% of the weight of the polymer.

EXAMPLE 2

Carbonylation runs under low water conditions were conducted in a one liter Hastalloy C autoclave to compare reaction rates between an unstabilized Rh system, a LiI stabilized system and the polymerically coordinated Rh catalyst described in Example 1. In all runs in this example the initial reactor water concentration was 2%, the agitator speed was 1500 rpm and the reactor temperature was 190° C. A critical parameter discovered in these autoclave experiments is that a relatively high agitator stirring speed is required to prevent the reactor from becoming CO mass transfer limited at the higher STYs. This phenomenon is specific to laboratory scale autoclaves and is not common to well designed commercial reactors.

The initial reactor contents were weighed into the autoclave and comparative runs were made to determine the relative kinetic activity of each catalyst system. In each case, a total of 200 grams of solution was used consisting of 38 grams of methyl iodide, 54 grams of methyl acetate, 4 grams of water, specified Rh concentrations (as $RhI_3$), specified Rh-polyvinylpyrrolidone concentrations, and 20.2 grams of LiI for the comparative run which contained LiI. The balance of the solution was acetic acid to obtain a total of 200 grams. In each case, the catalyst STY was determined by the CO uptake.

The autoclave was sealed, pressurized to 400 psig with CO and pressure checked for 15 minutes, after which the autoclave was slowly vented of CO to 150 psig and then heated to 190° C. Once the desired temperature was reached, the autoclave was further pressurized to 400 psig and the stirrer was started (1500 rpm). The rate of reaction was determined by monitoring the amount of CO consumed vs. time. For this particular one liter reaction using 200 gm of catalyst solution, it was found that a reactor temperature control scheme using a cooling coil containing silicon oil was necessary to remove the heat of reaction and maintain an isothermal 190° C. reaction temperature so that accurate kinetic measurements could be made.

The results of these experiments are shown in Table 1.

TABLE 1

| | STY (mole/1-hr) | Soluble Rh (ppm) |
|---|---|---|
| 472 ppm Rh ($RhI_3$) (unstabilized) | 3.3 | |
| 309 ppm Rh (polymer coordinated)* | 8.2 | 2 |
| 472 ppm Rh (polymer coordinated)* | 9.0 | 4 |
| 472 ppm Rh ($RhI_3$), 10.1% LiI | 12.3 | |
| 917 ppm Rh (polymer coordinated)* | 13.4 | 28 |

*Rhodium loaded polyvinylpyrrolidone catalyst for 309 ppm Rh = 2.9 wt % polymer catalyst, 472 ppm Rh = 4.4 wt % polymer catalyst, 917 ppm Rh = 8.5 wt % polymer catalyst of solution After the run, the polymer coordinated catalyst was separated by filtration from the solution and the residual soluble Rh was measured to illustrate the high degree of association between the polymer and the active Rh specie. This high level of association between the polymer and the Rh complex allows the use of higher Rh concentrations without suffering Rh precipitation or scaling problems common to the prior art processes.

EXAMPLE 3

The heterogeneous rhodium catalyst formed in Example 1 or insitu via addition of, for example, $RhI_3$ with cross-linked polyvinylpyrrolidone and methyl iodide (MeI), methyl acetate (MeAc) and acetic acid (HAc) was used to produce acetic anhydride. A 300 ml Hastelloy C autoclave was charged with 4.46 g cross-linked polyvinylpyrrolidone, 0.2237 g $RhI_3$, 55.73 g HAc, 27.12 g MeAc and 19.60 g MeI. The reactor did not contain any water nor was lithium iodide added. The mixture was heated to <190° C. under CO pressure, then the stirrer was started and the reaction pressure was set at 400 psig. The reaction temperature was adjusted to 190° C.± 1° C. The initial CO uptake was measured and the STY rate of $Ac_2O$ production was calculated to be ~1.07 mole/1 hr. In another run, previously used catalyst was charged with the HAc, MeAc and MeI and the reaction STY was calculated to be 1.09 mole/1 hr. In both runs, the amount of rhodium was fixed at approximately 475 ppm based on the solution weight. The reaction solution analyses of the reactor product liquid showed <2 ppm rhodium, which indicated no apparent rhodium leaching.

What is claimed is:

1. In a process for the carbonylation of an alcohol, ether or ester to products comprising a carboxylic acid, the anhydride thereof or coproduction of said carboxylic acid and anhydride thereof under carbonylation conditions in a reaction medium containing a rhodium catalyst and an iodide promoter, the improvement which comprises using as said rhodium catalyst a polymer containing pendant pyrrolidone groups, said pyrrolidone groups supporting a rhodium species.

2. The process of claim 1 wherein said polymer is a solid.

3. The process of claims 1 or 2 wherein said polymer is derived from vinylpyrrolidone.

4. The process of claim 2 wherein said polymer is polyvinylpyrrolidone cross-linked with divinylbenzene.

5. The process of claim 1 wherein said alcohol is methanol, said ester is methyl acetate and said products comprise acetic acid, acetic anhydride or coproduction of acetic acid and acetic anhydride.

6. The process of claim 1 wherein said iodide promoter comprises an alkyl iodide.

7. The process of claim 6 wherein said alkyl iodide promoter is methyl iodide.

8. The process of claim 1 wherein said reaction medium contains a finite amount of water up to less than 14 wt. % and 0 to less than 10 wt. % as equivalent molar lithium iodide of an iodide salt different than said iodide promoter.

9. The process of claim 8 wherein said iodide salt is lithium iodide.

10. The process of claim 8 wherein said reaction medium contains 0% of said iodide salt.

11. The process of claim 1 wherein said reaction medium contains greater than 500 ppm of rhodium.

12. The process of claim 11 wherein said reaction medium contains greater than 900 ppm rhodium.

13. The process of claim 12 wherein said reaction medium comprises 1000 to 5000 ppm rhodium.

14. The process of claim 2 wherein said catalyst comprises a mixture of a heterogeneous catalyst composed of said liquid or said solid polymer and a homogeneous rhodium catalyst.

15. In a process for the carbonylation of an alcohol, ether or ester to products comprising a carboxylic acid, anhydride thereof or coproduction of said carboxylic acid and anhydride thereof under carbonylation conditions in a reaction medium comprising a rhodium catalyst and an iodide promoter, the improvement which comprises using as said rhodium catalyst a polymer containing a group which supports a rhodium species, said polymer being stable at said carbonylation conditions including a temperature of at least 150° C., said reaction medium comprising greater than 500 ppm of said rhodium.

16. The process of claim 15 wherein said reaction medium comprises greater than 900 ppm rhodium.

17. The process of claim 16 wherein said reaction medium comprises from about 1000 to 5000 ppm rhodium.

18. The process of claim 15 wherein said polymer is stable at temperatures of at least 150° C.

19. The process of claim 15 wherein said polymer is a liquid homogeneous with said reaction medium, a liquid heterogeneous with respect to said reaction medium or a solid.

20. The process of claim 15 wherein said polymer is a solid.

21. The process of claim 1 wherein said rhodium catalyst is heterogeneous with respect to said reaction medium.

22. The process of claim 1 wherein said rhodium catalyst is homogeneous with respect to said reaction medium.

23. The process of claim 1 wherein said reaction medium contains a finite amount of water up to less than 14 wt. % and up to 20 wt. % as equivalent molar lithium iodide of an iodide salt different than said iodide promoter.

24. The process of claim 2 wherein said reaction medium further contains up to 20 wt. % as equivalent molar lithium iodide of an iodide salt other than said promoter.

25. The process of claim 15 wherein said reaction medium contains a finite amount of water up to less than 14 wt. % and up to 20 wt. % as equivalent molar lithium iodide of an iodide salt different than said iodide promoter.

* * * * *